United States Patent
Rajamannan

(10) Patent No.: US 6,660,260 B1
(45) Date of Patent: *Dec. 9, 2003

(54) BIOPROSTHETIC HEART VALVES

(75) Inventor: Nalini M. Rajamannan, Rochester, MN (US)

(73) Assignee: Mayo Foundation for Medical Education and Research, Rochester, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/399,704

(22) Filed: Sep. 21, 1999

(51) Int. Cl.$^7$ .................. A61K 48/00; A61F 2/00; A61F 2/24; C12N 15/63; C12N 15/86

(52) U.S. Cl. .................. 424/93.21; 424/423; 623/2; 435/455; 435/456; 435/320.1

(58) Field of Search .................. 514/44; 435/69.1, 435/370.1, 1.1, 1.31, 455, 456, 320.1, 455.1, 456.1; 536/23.1, 23.2; 424/423.1, 93.21, 423; 623/2, 11

(56) References Cited

U.S. PATENT DOCUMENTS

| | | | |
|---|---|---|---|
| 4,477,930 A | | 10/1984 | Totten et al. |
| 4,762,842 A | | 8/1988 | Cohen et al. |
| 5,650,447 A | * | 7/1997 | Keefer et al. .......... 514/772.4 |
| 5,797,870 A | | 8/1998 | March et al. |
| 5,855,620 A | * | 1/1999 | Bishopric et al. .......... 623/11 |
| 5,880,102 A | | 3/1999 | George et al. |
| 5,928,281 A | | 7/1999 | Huynh et al. |
| 5,935,163 A | | 8/1999 | Gabbay |
| 6,060,640 A | | 5/2000 | Pauley et al. |
| 6,087,479 A | * | 7/2000 | Stamler et al. .......... 530/363 |
| 6,193,749 B1 | * | 2/2001 | Schroeder et al. ........ 623/1.42 |

OTHER PUBLICATIONS

Ngo et al. Computational complexity, protein structure prediction, and the Levinthal paradox. In: The protein folding problem and teritary structure prediction (Merz et al., eds.), Birkhauser, Boston, pp. 491–495, 1994.*

Rudinger, J. Characteristics of the amino acids as components of a peptide hormone sequence. In: Peptide hormones (Parsons, J.A., ed.), University Park Press, Baltimore, pp. 1–7, 1976.*

Guillot et al, Gene therapy in transplantation in the year 2000: moving towards clinical applications?, 2000, Gene Therapy, vol. 7, pp. 14–19.*

Eck et al., Gene-based therapy, 1996, Goodman & Gilliman's The Pharmacological Basis of Therapeutics, pp. 77–101.*

Lee et al., *Circulation*, 2000, 101:2345–2348.

Angell et al., *J. Thoracic Cardiovasc. Surg.*, 1989, 98(1):48–56.

Clancy et al., *J. Clin. Invest.*, 1997, 100(7):1789–1796.

Cooke et al., *Annu. Rev. Med.*, 1997, 48:489–509.

Dayan et al., *Histochemistry*, 1989, 93(1):27–29.

Dzau et al., *Proc. Natl. Acad. Sci. USA*, 1996, 93:11421–11425.

Gibbons et al., *Science*, 1996, 272:689–693.

Hernandez-Perera et al., *J. Clin. Invest.*, 1998, 101(12):2711–2719.

Johnson et al., *J. Mol. Cell. Cardiol.*, 1987, 19(12):1185–1193.

Kullo et al., *Arterio, Thromb. Vascul. Biol.*, 1997, 17(11):2405–2412.

Mann et al., *J. Clin. Invest.*, 1997, 99(6):1295–1301.

Mohler III et al., *Arteriosclerosis, Thrombosis, and Vascular Biology*, 1997, 17(3):547–552.

Myers et al., *Arterio. Thromb. Vascul. Biol.*, 1998, 18(5):717–722.

O'Brien et al., *J. Thoracic Cardiovasc. Surg.*, 1987, 94(6):812–823.

Onoue et al., *Stroke: Journal of the American Heart Association*, 1998, 29(9)1959–1965.

Rizvi et al., *J. Mol. Cell. Cardiol.*, 1997, 29(7):1779–1789.

Tsutsui et al., *Arterio. Thromb. Vascul. Biol.*, 1998, 18(8):1231–1241.

von der Leyen et al., *Proc. Natl. Acad. Sci. USA*, 1995, 92(4):1137–1141.

*Heart Disease*, ed. E. Braunwald, 4$^{th}$ Edition, p. 1035–1036 (1992).

* cited by examiner

*Primary Examiner*—David Guzo
*Assistant Examiner*—Quang Nguyen
(74) *Attorney, Agent, or Firm*—Fish & Richardson P.C., P.A.

(57) ABSTRACT

The invention provides methods and materials related to heart valves and the treatment of valvular heart disease. Specifically, the invention provides non-murine heart valve cells and heart valve cusps as well as methods for making heart valves. The invention also provides methods and materials for (1) slowing heart valve degeneration, thrombosis, and calcification, (2) treating carcinoid heart disease, (3) identifying inhibitors of heart valve degeneration, thrombosis, and calcification, and (4) determining the safety of drugs.

20 Claims, 2 Drawing Sheets

BIOPROSTHETIC HEART VALVES

BACKGROUND

1. Technical Field

The invention relates to bioprosthetic heart valves and the treatment of valvular heart disease.

2. Background Information

The heart is a hollow, muscular organ that circulates blood throughout an animal's body by contracting rhythmically. In mammals, the heart has four-chambers situated such that the right atrium and ventricle are completely separated from the left atrium and ventricle. Normally, blood flows from systemic veins to the right atrium, and then to the right ventricle from which it is driven to the lungs via the pulmonary artery. Upon return from the lungs, the blood enters the left atrium, and then flows to the left ventricle from which it is driven into the systematic arteries.

Four main heart valves prevent the backflow of blood during the rhythmic contractions: the tricuspid, pulmonary, mitral, and aortic valves. The tricuspid valve separates the right atrium and right ventricle, the pulmonary valve separates the right atrium and pulmonary artery, the mitral valve separates the left atrium and left ventricle, and the aortic valve separates the left ventricle and aorta. Generally, patients having an abnormality of a heart valve are characterized as having valvular heart disease.

A heart valve can malfunction either by failing to open properly (stenosis) or by leaking (regurgitation). For example, a patient with a malfunctioning aortic valve can be diagnosed with either aortic valve stenosis or aortic valve regurgitation. In either case, valve replacement by surgical means is a possible treatment. Replacement valves can be autografts, allografts, or xenografts as well as mechanical valves or valves made partly from pig valves. Interestingly, cryopreserved allografts remain viable within the recipient patient for many years after transplantation. Unfortunately, replacement valves are susceptible to problems such as degeneration, thrombosis, and calcification.

SUMMARY

The invention involves methods and materials related to heart valves and the treatment of valvular heart disease. Specifically, the invention provides heart valve cells and heart valve cusps as well as methods for making heart valves. The invention also provides methods and materials for (1) slowing heart valve degeneration, thrombosis, and calcification, (2) treating carcinoid heart disease, (3) identifying inhibitors of heart valve degeneration, thrombosis, and calcification, and (4) determining the safety of drugs.

The invention is based on the discovery that heart valve cells expressing a polypeptide having nitric oxide synthase activity do not exhibit characteristics indicative of heart valve calcification and degeneration. Specifically, heart valve cells containing nucleic acid that encodes a polypeptide having nitric oxide synthase activity exhibit, in response to a valvular heart disease-promoting stimulus, a different extracellular matrix profile than that exhibited by similar cells lacking that nucleic acid. The molecular makeup of a heart valve's extracellular matrix can be an important factor that determines the degree of heart valve calcification and degeneration. For example, significant expression of osteopontin, a polypeptide abundant in bone matrix, can lead to significant tissue calcification. Heart valve cells containing nucleic acid that encodes a polypeptide having nitric oxide synthase activity also exhibit, in response to a valvular heart disease-promoting stimulus, less proliferation and apoptosis than the proliferation and apoptosis exhibited by similar cells lacking that nucleic acid. The level of heart valve cell proliferation and apoptosis can correlate with the degree of heart valve calcification and degeneration. For example, significant proliferation and apoptosis of heart valve cells can lead to heart valve thickening, and thus heart valve malfunction and degeneration. It is noted that tissue thickening occurs presumably because cell proliferation out paces apoptosis over time. The heart valve cells and cusps described herein can be used to make bioprosthetic heart valves having a reduced susceptibility or prolonged resistance to degeneration, thrombosis, and calcification. Clearly, such bioprosthetic heart valves would be useful in any type of heart valve replacement procedure.

The invention also is based on the discovery that serotonin receptor antagonists (e.g., $5HT_{1B}$ receptor antagonists) can inhibit serotonin-induced proliferation of heart valve cells from patients diagnosed with carcinoid heart disease. Thus, serotonin receptor antagonists can be used to treat carcinoid heart disease. Further, the methods and materials used to identify serotonin receptor antagonists as a treatment for carcinoid heart disease also can be used to identify drugs for the treatment of other valvular heart diseases as well as test the safety of any drug designed for human use. Clearly, identifying new valvular heart disease treatments and determining drug safety in general will greatly improve overall human health care.

In general, one aspect of the invention features a non-murine heart valve cell (e.g., an endothelial cell or myocyte) containing an exogenous nucleic acid that encodes a polypeptide having nitric oxide synthase activity (e.g., endothelial nitric oxide synthase).

In another embodiment, the invention features an isolated heart valve cusp where a cell of the cusp contains an exogenous nucleic acid that encodes a polypeptide having nitric oxide synthase activity (e.g., endothelial nitric oxide synthase). The cell can be a porcine or human cell.

Another embodiment of the invention features a method for making a bioprosthetic heart valve. The method includes obtaining a heart valve cusp and introducing nucleic acid into a cell of the cusp, where the nucleic acid encodes a polypeptide having nitric oxide synthase activity (e.g., endothelial nitric oxide synthase). The cell can be a porcine or human cell. The nucleic acid can be introduced into the cell via adenoviral-mediated nucleic acid transfer. The nucleic acid can be integrated into the genome of the cell. The method can include fixing the cusp, and the fixation step can occur after the introduction step. The method can include freezing the cusp, and the freezing step can occur after the introduction step.

In another aspect, the invention features a method for slowing the degeneration of a heart valve within a non-murine mammal. The method includes introducing nucleic acid encoding a polypeptide having nitric oxide synthase activity into a cell of the heart valve such that the polypeptide is expressed. The introduction step can be performed in vitro. The heart valve can be an autograft, allograft, or xenograft. The method can include administering an inhibitor of hydroxymethylglutaryl coA reductase activity to the mammal. The inhibitor can be pravastatin, atorvastatin, simvastatin, or lovastatin.

In another embodiment, the invention features a method for slowing heart valve degeneration. The method includes identifying a mammal at risk of developing heart valve degeneration, and administering an inhibitor of hydroxymethylglutaryl coA reductase activity to the mammal. The mammal can contain a heart valve replacement. The mammal can have congenital valvular disease or bicuspid valvular disease.

Another aspect of the invention features a method for treating carcinoid heart disease in a mammal. The method includes administering a serotonin receptor antagonist to the mammal. The antagonist can be specific for a $5HT_{1B}$ receptor. The antagonist can contain a β-blocker. The antagonist can be pindolol.

Another aspect of the invention features a method for identifying an inhibitor of heart valve degeneration. The method includes contacting heart valve cells with a stimulant such that the cells proliferate, contacting the cells with a test compound, and determining if the test compound reduced the proliferation of the cells, where the reduction of proliferation indicates that the test compound is an inhibitor of heart valve degeneration.

In another embodiment, the invention features a method for determining the safety of a drug. The method includes contacting heart valve cells with the drug, and determining if the drug induced proliferation of the cells, where the induction of proliferation indicates that the drug promotes heart valve degeneration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
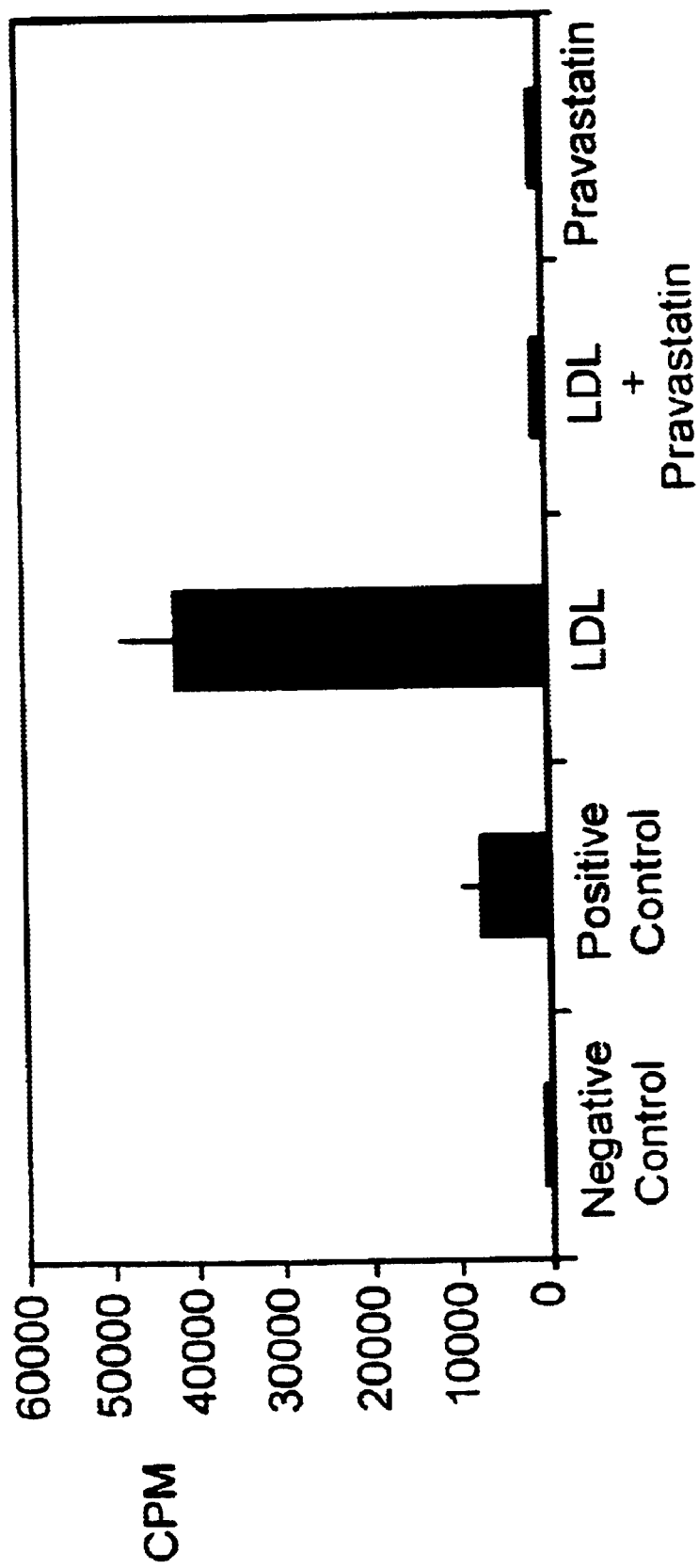
FIG. 1 is a bar graph plotting the counts per minute (cpm) for valvular cells treated with serum-free media (negative control), media with 10% fetal bovine serum (positive control), LDL alone, LDL plus pravastatin, or pravastatin alone.

The invention provides methods and materials related to heart valves and the treatment of valvular heart disease. Specifically, the invention provides non-murine heart valve cells and heart valve cusps as well as methods for making heart valves. The invention also provides methods and materials for (1) slowing heart valve degeneration, thrombosis, and calcification, (2) treating carcinoid heart disease, (3) identifying inhibitors of heart valve degeneration, thrombosis, and calcification, and (4) determining the safety of drugs.

1. Heart Valve Cells

A non-murine heart valve cell of the invention contains exogenous nucleic acid that encodes a polypeptide having nitric oxide synthase activity. Such heart valve cells can be used to make bioprosthetic heart valves with significant durability since these cells produce a favorable extracellular matrix. Briefly, an extracellular matrix is any material produced by cells and secreted into the surrounding medium (e.g., the noncellular portion of animal tissue). In broad terms, there are three major components of an extracellular matrix: fibrous elements (e.g., collagen, elastin, and reticulin), link polypeptides (e.g., fibronectin and laminin), and space filling molecules (e.g., glycosaminoglycans). Although an extracellular matrix is produced by cells, it can dramatically influence the behavior of tissue cells. In short, the properties of an extracellular matrix have a large influence on the properties of the tissue. Thus, the molecular makeup of a heart valve's extracellular matrix is an important component determining thrombosis as well as heart valve degeneration and calcification.

As described herein, non-murine heart valve cells containing exogenous nucleic acid that encodes a polypeptide having nitric oxide synthase activity produce a different set of extracellular matrix molecules than those produced by similar cells lacking exogenous nucleic acid that encodes a polypeptide having nitric oxide synthase activity. For example, unmodified heart valve cells exposed to harmful stimuli such as hyperlipidemia produce fibronectin and osteopontin, while heart valve cells of the invention produce little, if any, fibronectin or osteopontin in response to hyperlipidemia. Thus, any non-murine heart valve cell can be given exogenous nucleic acid that encodes a polypeptide having nitric oxide synthase activity to change the molecular makeup of the extracellular matrix produced by a heart valve cell.

In addition, a heart valve cell within the scope of the invention can be used to make bioprosthetic heart valves with significant durability since such cells do not proliferate excessively in response to harmful stimuli such as hyperlipidemia. Briefly, hyperlipidemia refers to an elevated concentration of lipids (e.g., cholesterol, triglycerides, and lipoproteins) in plasma. As described herein, heart valve cells exposed to hyperlipidemic conditions exhibit excessive proliferation and apoptosis that can lead to a malfunctioning heart valve. However, non-murine heart valve cells containing exogenous nucleic acid encoding a polypeptide having nitric oxide synthase activity exhibit little, if any, proliferation or apoptosis in response to harmful stimuli. Thus, any non-murine heart valve cell can be given exogenous nucleic acid that encodes a polypeptide having nitric oxide synthase activity to inhibit heart valve cell proliferation and apoptosis.

A non-murine heart valve cell is any non-murine cell obtained from heart valve tissue or any non-murine cell that has been cultured in such a way as to develop characteristics indistinguishable from those of a cell obtained from heart valve tissue. For example, a non-murine heart valve cell can be, without limitation, an endothelial cell or myocyte obtained from human heart valve tissue. In addition, a non-murine heart valve cell can be, without limitation, a cell derived from a human stem cell that was cultured such that it resembles an endothelial cell or myocyte obtained from human heart valve tissue. It is important to note that a heart valve cell can be from any non-murine species having heart valve tissue including, without limitation, mammals such as pigs, cows, horses, sheep, goats, monkeys, and humans. The term "murine" as used herein refers to all species grouped within the Murinae taxon. Thus, all porcine cells would be considered non-murine cells. In addition, a heart valve cell can be obtained from any heart valve including the tricuspid, pulmonary, mitral, and aortic valves of a non-murine mammal. It also is important to note that the heart valve cells of the invention can be in any physical state. For example, a heart valve cell of the invention can be a cell within an organism's body, a cell maintained in tissue culture, or a cell that is or has been fixed, frozen, or otherwise treated. Thus, a fixed non-murine heart valve cell containing nucleic acid encoding a polypeptide having nitric oxide synthase activity that is stored at −70° C. is within the scope of the invention. When fixing cells, any fixative (e.g., glutaraldehyde under high pressure) can be used. When freezing cells, any temperature below freezing (e.g., 0, −20, and −70° C.) can be used. In addition, those skilled in the art will appreciate that media used to freeze cells will normally contain ingredients that help promote cell viability during freezing and thawing procedures such as dimethyl sulfoxide.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "exogenous" as used herein with reference to nucleic acid and a particular cell refers to any nucleic acid that does not originate from that particular cell as found in nature. Thus, all non-naturally occurring nucleic acid are considered to be exogenous to a cell once introduced into the cell. It is important to note that non-naturally occurring nucleic acid can contain nucleic acid sequences or fragments of nucleic acid sequences that are found in nature provided the nucleic acid as a whole does not exist in nature. For example, a nucleic acid containing a genomic DNA sequence within an expression vector is considered to be a non-naturally occurring nucleic acid, and thus is considered to be exogenous to a cell once introduced into the cell, since that nucleic acid as a whole (genomic DNA plus vector DNA) does not exist in nature. Thus, any vector, autonomously replicating plasmid, or virus (e.g., retroyirus, adenovirus, or herpes virus) that as a whole does not exist in nature is considered to be a non-naturally-occurring nucleic acid. It follows that genomic DNA fragments produced by PCR or restriction endonuclease treatment as well as cDNA's are considered to be a non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is considered to be a non-naturally occurring nucleic acid.

It is also important to note that a nucleic acid that is naturally occurring can be exogenous to a particular cell. For example, an entire chromosome isolated from a cell of person X would be considered an exogenous nucleic acid with respect to a cell of person Y once that chromosome is introduced into Y's cell.

Any nucleic acid that encodes a polypeptide having nitric oxide synthase activity (i.e., EC 1.14.13.39) can be used as described herein. Polypeptides having nitric oxide synthase activity include, without limitation, nitric oxide synthase polypeptides designated as being type 1, 2, or 3 (i.e., NOS1, NOS2, or NOS3). For example, a nucleic-acid encoding NOS1, NOS2, or NOS3 can be given to a non-murine heart valve cell as described herein. In addition, a polypeptide having nitric oxide synthase activity can be a polypeptide that is either naturally-occurring or non-naturally-occurring. A naturally-occurring polypeptide is any polypeptide having an amino acid sequence as found in nature, including wild-type and polymorphic polypeptides. Such naturally-occurring polypeptides can be obtained from any species including, without limitation, homo sapiens as well as other mammalian species such as murine, porcine, and bovine species and non-mammalian species such as insect (e.g., Drosophila and Anopheles), fish (e.g., goldfish), and bird (e.g., chicken) species. For example, rat polypeptides having nitric oxide synthase activity can have an amino acid sequence as set forth in the GenBank® submissions with Accession Numbers P29476, Q06518, Q62600, and AAC52782. Additional polypeptides having nitric oxide synthase activity can include, without limitation, bovine polypeptides (e.g., Accession Numbers P29473, 742990, 145946, and AAB22708), mouse polypeptides (e.g., Accession Numbers JN0609, P29477, and AAC52766), rabbit polypeptides (e.g., Accession Number AAB68663), guinea pig polypeptides (e.g., Accession Numbers AAD29751 and AAD29752), chicken polypeptides (e.g., Accession Number Q90703), dog polypeptides (e.g., Accession Number AAD39340), tobacco hornworm polypeptides (e.g., Accession Number AAC61262), pig polypeptides (e.g., Accession Numbers AAB39539), and human polypeptides (e.g., Accession Numbers P29475, AAB60654, P35228, P29474, AAB49040, AAA36376, S28878, JX0345, CAA53950, BAA05652, and AAA36364).

A non-naturally-occurring polypeptide is any polypeptide having an amino acid sequence that is not found in nature. Thus, a non-naturally-occurring polypeptide can be a mutated version of a naturally-occurring polypeptide, or an engineered polypeptide. For example, a non-naturally-occurring polypeptide having nitric oxide synthase activity can be a mutated version of a naturally-occurring polypeptide having nitric oxide synthase activity that retains at least some nitric oxide synthase activity. Possible mutations include, without limitation, deletions, insertions, and base substitutions, as well as combinations of deletions, insertions, and base substitutions. Any method including common molecular cloning techniques (e.g., site-directed mutageneses) can be used to create a mutated version of a naturally-occurring polypeptide that retains at least some nitric oxide synthase activity.

Nucleic acid encoding a polypeptide having nitric oxide synthase activity can be identified and obtained using any method. For example, a nucleic acid encoding a nitric oxide synthase polypeptide having an amino acid sequence as set forth in GenBank® Accession Number CAA53950 can be obtained using PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

In addition, nucleic acid and amino acid databases (e.g., GenBank®) can be used to identify a nucleic acid sequence that encodes a polypeptide having nitric oxide synthase activity. Briefly, any nucleic acid or amino acid sequence having some homology (e.g., at least about 30, 40, 50, 60, 70, 80, 90, 95, or 99% identity) to a known nitric oxide synthase sequence can be used as a query to search GenBank®. Such searches can be performed over the Internet at, for example, www.ncbi.nlm.nih.gov.

Further, nucleic acid hybridization techniques can be used to identify and obtain nucleic acid that encodes a polypeptide having nitric oxide synthase activity. Briefly, any nucleic acid known to encode a polypeptide having nitric oxide synthase activity, or fragment thereof, can be used as a probe to identify a similar nucleic acid by hybridization under conditions of low to high stringency. Such similar nucleic acid then can be isolated, sequenced, and analyzed to verify that the encoded polypeptide exhibits nitric oxide synthase activity.

In general, high stringency conditions can be used to identify nucleic acid having a high degree of homology to a probe. High stringency conditions can include the use of a denaturing agent such as form amide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.5), 0.1% sodium pyrophosphate, 5×Denhardt's solution, sonicated salmon sperm DNA (50 µg/ml), 0.1% sodium lauryl sulfate (SDS), and 10% dextran sulfate at 42° C., with washes at 42° C. in 0.2×SSC and 0.1% SDS. Alternatively, low ionic strength and high temperature can be used for washing, for example, 0.1×SSC (0.015 M NaCl/0.0015 M sodium citrate), 0.1% SDS at 65° C.

Moderate stringency conditions can be used to identify nucleic acid having a moderate degree of homology to a probe. Moderate stringency conditions can include the use of higher ionic strength and/or lower temperatures for washing of the hybridization membrane, compared to the ionic strength and temperatures used for high stringency hybridization. For example, a wash solution of 4×SSC (0.06 M NaCl/0.006 M sodium citrate), 0.1% SDS can be used at 50° C., with a last wash in 1×SSC at 65° C. Alternatively, a hybridization wash in 1×SSC at 37° C. can be used.

Low stringency conditions can be used to identify nucleic acid having a low degree of homology to a probe. Low stringency conditions can include the use of higher ionic strength and/or lower temperatures for washing of the hybridization membrane, compared to the ionic strength and temperatures used for moderate stringency hybridization. For example, a wash solution of 4×SSC (0.06 M NaCl/0.006 M sodium citrate), 0.1% SDS can be used at 37° C., with a last wash in 1×SSC at 45° C. Alternatively, a hybridization wash in 2×SSC at 37° C. can be used.

Hybridization can be done by Southern or Northern analysis to identify a DNA or RNA sequence, respectively, that hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence within the GenBank® submission having Accession Number D26607 or M93718 can be used to identify a nucleic acid identical or similar to the nucleic acid sequence encoding human endothelial nitric oxide synthase. In addition, probes longer or shorter than 20 nucleotides can be used.

The exogenous nucleic acid contained within a cell of the invention can be maintained within that cell in any form. For example, exogenous nucleic acid can be integrated into the genome of the cell or maintained in an episomal state. In other words, a cell of the invention can be a stable or transient transformant.

In addition, any method can be used to introduce an exogenous nucleic acid into a cell. In fact, many methods for introducing nucleic acid into cells, whether in vivo or in vitro, are well known to those skilled in the art. For example, calcium phosphate precipitation, electroporation, particle bombardment, heat shock, lipofection, microinjection, and viral-mediated nucleic acid transfer are common methods for introducing nucleic acid into cells. Thus, well known adenovirus-mediated nucleic acid transfer methods such as those described by Berkner et al. (*Nucleic Acids Res.*, 11:6003–6020 (1983)), van Doren et al. (*Mol. Cell. Biol.*, 4:1653–1656 (1984)), Ghosh-Choudhury et al. (*Biochem. Biophys. Res. Commun.*, 147:964–973 (1987)), McGrory et al. (*Virology*, 163:614–617 (1988)), and Gluzman et al. (In: Eurkaryotic Viral Vectors, Ed. Gluzman, Y. pages 187–192, Cold Spring Harbor Laboratory (1982)) can be used to introduce exogenous nucleic acid encoding a polypeptide having nitric oxide synthase activity into a heart valve cell. In addition, naked DNA can be delivered directly to cells in vivo as describe elsewhere (U.S. Pat. No. 5,580,859 and U.S. Pat. No. 5,589,466 including continuations thereof). Further, nucleic acid can be introduced into cells by generating transgenic animals such as transgenic pigs, goats, sheep, cows, horses, dogs, cats, rabbits, baboon, monkeys, and chimpanzees. Several techniques known in the art can be used to introduce nucleic acid into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA*, 82:6148–6152 (1985)); gene transfection into embryonic stem cells (Gossler A et al., *Proc Natl Acad Sci USA* 83:9065–9069 (1986)); gene targeting into embryonic stem cells (Thompson et al., *Cell*, 56:313–321 (1989)); nuclear transfer of somatic nuclei (Schnieke AE et al., *Science* 278:2130–2133 (1997) and Wilmut I et al., *Nature* 385:810–13 (1997)); and electroporation of embryos.

For a review of techniques that can be used to generate and assess transgenic animals, skilled artisans can consult Gordon (*Intl. Rev. Cytol.*, 115:171–229 (1989)), and can obtain additional guidance from, for example: Hogan et al., "Manipulating the Mouse Embryo" Cold Spring Harbor Press, Cold Spring Harbor, N.Y. (1986); Krimpenfort et al., *Bio/Technology*, 9:844–847 (1991); Palmiter et al., *Cell*, 41:343–345 (1985); Kraemer et al., "Genetic Manipulation of the Early Mammalian Embryo" Cold Spring Harbor Press, Cold Spring Harbor, N.Y. (1985); Hammer et al., *Nature*, 315:680–683 (1985); Purscel et al., *Science*, 244:1281–1288 (1986); Wagner et al., U.S. Pat. No. 5,175,244; and Krimpenfort et al., U.S. Pat. No. 5,175,384.

Methods of identifying cells that contain exogenous nucleic acid also are well known to those skilled in the art. Such methods include, without limitation, PCR and nucleic acid hybridization techniques such as Northern and Southern analysis. For example, a nucleic acid fragment from a known nitric oxide synthase nucleic acid sequence can be used as a probe in a Southern blot analysis to determine if a particular cell contains nucleic acid corresponding to that probe.

In addition to containing an exogenous nucleic acid that encodes a polypeptide having nitric oxide synthase activity, a cell of the invention can express the encoded polypeptide having nitric oxide synthase activity. Any method can be used to express a polypeptide from an exogenous nucleic acid. For example, a nucleic acid can be constructed such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like.

Many methods can be used to identify cells that contain exogenous nucleic acid and express the encoded polypeptide. Such methods include, without limitation, PCR, RT-PCR, nucleic acid hybridization techniques, immunohistochemistry, and biochemical techniques. Briefly, RT-PCR techniques and Northern analysis can be used to assess the expression of nitric oxide synthase mRNA, while immunocytochemistry using anti-nitric oxide synthase antibodies can be used to assess the expression of nitric oxide synthase polypeptide. For example, detection of nitric oxide synthase-immunoreactivity after introduction of an exogenous nucleic acid that encodes a polypeptide having nitric oxide synthase activity into a cell that does not normally express a nitric oxide synthase polypeptide can indicate that cell not only contains the introduced exogenous nucleic acid but also expresses the encoded nitric oxide synthase polypeptide from that introduced exogenous nucleic acid. Likewise, biochemical detection of nitric oxide synthase activity within a cell can indicate that particular cell expresses the encoded nitric oxide synthase polypeptide.

2. Heart Valve Cusps

The invention also provides heart valve cusps that contain a cell (e.g., a non-murine cell) with exogenous nucleic acid encoding a polypeptide having nitric oxide synthase activity. Such heart valve cusps can be used to make heart valves (e.g., bioprosthetic heart valves) that can replace native heart valves within mammals (e.g., humans). It is important to note that the heart valve cusps of the invention can be used to make any type of heart valve including valves having two or three cusps (e.g., bicuspid and tricuspid heart valves). In addition, heart valve cusps can be obtained from any non-murine species including, without limitation, mammals such as pigs, cows, horses, sheep, goats, monkeys, and humans. Thus, a heart valve cusp that is used to replace a native cusp within a mammal can be an autograft, allograft, or xenograft. The term "autograft" refers to a surgical graft of tissue taken from one part of the body and placed in another site of the same individual. The term "allograft" refers to a surgical graft of tissue taken from one individual's body and placed into another individual's body with the two individuals being allogeneic at one or more loci such as a histocompatibility loci. The term "xenograft" refers to a surgical graft of tissue taken from one species and placed into an individual of a different species.

A heart valve cusp of the invention can be an isolated heart valve cusp. The term "isolated" as used herein with reference to a heart valve cusp refers to any heart valve cusp that has been removed from an organism's heart. For example, a heart valve cusp that has been surgically removed from a pig's heart is an isolated heart valve cusp. It will be understood that a heart valve cusp that was removed from a pig's heart and placed within a human patient's heart is an isolated heart valve cusp since that cusp has been removed from a pig's heart.

It is noted that a heart valve cusp of the invention can be a cusp that is not removed from an organism's body. In other words, exogenous nucleic acid encoding a polypeptide having nitric oxide synthase activity can be introduced into an organism's heart valve cusp in vivo or in vitro. For example, a human patient can be given an adenoviral vector such that a cell of a heart valve cusp acquires nucleic acid that encodes a polypeptide having nitric oxide synthase activity. In this case, the expression to the polypeptide having nitric oxide synthase activity can lead to significant heart valve durability. In addition, the human patient can be given an inhibitor of hydroxymethylglutaryl coA reductase activity (i.e., EC 1.1.1.34) such as pravastatin, atorvastatin, simvastatin, or lovastatin. As described herein, administration of an inhibitor of hydroxymethylglutaryl coA reductase activity can reduce heart valve calcification and degeneration within a mammal.

Like the cells of the invention, a heart valve cusp can be in any physical state. For example, a heart valve cusp of the invention can be within an organism's body, maintained in tissue culture, or fixed, frozen, or otherwise treated. Thus, heart valve cusps that have been removed from an organism's body as well as those within an organism's body are within the scope of the invention provided they contain a non-murine cell having exogenous nucleic acid that encodes a polypeptide having nitric oxide synthase activity.

It is noted that any number of the cells constituting a heart valve cusp from a single cell to all the cells can contain exogenous nucleic acid encoding a polypeptide having nitric oxide synthase activity. For example, about one, two, five, ten, or fifty percent of the cells of a heart valve cusp can contain exogenous nucleic acid encoding a polypeptide having nitric oxide synthase activity.

3. Use of Hydroxymethylglutaryl coA Reductase Inhibitors

The invention also provides methods for slowing the onset, or rate of progression, of heart valve degeneration, thrombosis, and calcification. In addition, the provided methods can reduce a mammal's susceptibility to, or prolong a mammal's resistance against, heart valve degeneration, thrombosis, and calcification. These methods include (a) identifying a mammal at risk of developing heart valve degeneration, thrombosis, or calcification, and (b) administering an inhibitor of hydroxymethylglutaryl coA reductase activity. Mammals at risk of developing heart valve degeneration, thrombosis, or calcification include, without limitation, mammals that have received heart valve replacement surgery as well as those mammals having congenital valvular disease (e.g., bicuspid valvular disease). Such mammals can be identified using standard clinical diagnostic techniques (e.g., echocardiography and cardiac catheterization). In addition, medical history records can be used to identify patients at risk of developing heart valve degeneration, thrombosis, or calcification. For example, medical history records can be used to identify patients having had heart valve replacement surgery while between the age of 30 and 50 years since such patients are at risk of developing heart valve degeneration, thrombosis, or calcification.

Once a mammal in need of treatment is identified, an inhibitor of hydroxymethylglutaryl coA reductase activity can be administered. Although not limited to any particular mode of action, administration of an inhibitor of hydroxymethylglutaryl coA reductase activity presumably causes an increase in nitric oxide synthase activity within valvular tissue. As described herein, an increase in nitric oxide synthase activity within valvular tissue can alter the molecular makeup of the heart valve's extracellular matrix as well as inhibit heart valve cell proliferation and apoptosis normally induced by harmful stimuli. Inhibitors of hydroxymethylglutaryl coA reductase activity include, without limitation, statin drugs such as pravastatin, atorvastatin, simvastatin, and lovastatin.

Any method can be used to determine if hydroxymethylglutaryl coA reductase activity was inhibited. For example, the level of expression of a particular nitric oxide synthase enzyme can be determined by measuring mRNA or polypeptide levels within a tissue sample. Moreover, clinical methods that can assess the degree of hydroxymethylglutaryl coA reductase or nitric oxide synthase activity can be used to determine whether hydroxymethylglutaryl coA reductase activity was inhibited.

Typically, a pharmaceutically effective amount of an inhibitor of hydroxymethylglutaryl coA reductase activity is administered to a mammal in need of treatment. A pharmaceutically effective amount of an inhibitor of hydroxymethylglutaryl coA reductase activity refers to any amount that does not cause significant toxicity to the host and inhibits hydroxymethylglutaryl coA reductase activity. Such an amount can be determined by assessing the clinical symptoms of a patient before and after administering a fixed amount of a particular material. In addition, the pharmaceutically effective amount of a particular material administered to a host can be adjusted according to the host's response and desired outcomes. Significant toxicity can vary for each particular patient and depends on multiple factors including, without limitation, the patient's age, tolerance to pain, and disease state.

In addition, any of the materials described herein can be administered to any part of the host's body including, without limitation, the blood stream, lungs, intestines, and the like. Thus, an inhibitor of hydroxymethylglutaryl coA reductase activity can be administered by intravenous injection, inhalation, or oral administration. For example, an aerosol preparation containing an inhibitor of hydroxymethylglutaryl coA reductase activity can be given to a patient by inhalation. It is noted that the duration of treatment with any of the materials described herein can be any length of time from as short as one day to as long as a lifetime (e.g., many years). For example, an inhibitor of hydroxymethylglutaryl coA reductase activity can be administered at some frequency over a period of ten years. It is also noted that the frequency of treatment can be variable. For example, an inhibitor of hydroxymethylglutaryl coA reductase activity can be administered once (or twice, three times, etc.) daily, weekly, monthly, or yearly.

Preparations for administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water as well as alcohol, saline, and buffered solutions. Preservatives, flavorings, and other additives such as, for example, antimicrobials, anti-oxidants, chelating agents, inert gases, and the like may also be present.

4. Treating Carcinoid Heart Disease

Carcinoid heart disease refers to a cardiac manifestation of malignant carcinoid syndrome. Briefly, carcinoid heart disease is a unique form of fibrosis involving primarily the endocardium of the right heart. In general, fibrous deposits tend to cause constriction of the tricuspid and pulmonary heart valves. Mammals having carcinoid heart disease can be identified using common medical diagnostic techniques. For example, echocardiography can be used to identify human patients that have carcinoid heart disease. In addition, 5-hydroxyindole acetic acid (5-HIAA) levels within urine can be measured to identify mammals having a carcinoid tumor. Typically, an elevated level of 5-HIAA in a patient's urine indicates the presence of a carcinoid tumor. It is noted that the normal range of 5-HIAA within urine collected for a 24 hour time period is about 0.0 mg to about 6.0 mg (i.e., about 0–6 mg 5-HIAA in urine per 24 hours).

As described herein, administration of a serotonin receptor inhibitor (e.g., a $5HT_{1B}$ receptor inhibitor) can reduce serotonin-induced proliferation of valvular tissue. Briefly, serotonin was found to induce proliferation of heart valve cells in a $5HT_{1B}$ selective manner, indicating the involvement of $5HT_{1B}$ receptor activity in the proliferation process. Thus, carcinoid heart disease can be treated by administering a serotonin receptor inhibitor. Such inhibitors include, without limitation, β-blockers such as pindolol, meththiotepin, metoprolol, and paldolol.

Typically, a pharmaceutically effective amount of a serotonin receptor inhibitor is administered to a mammal in need of treatment. A pharmaceutically effective amount of a serotonin receptor inhibitor refers to any amount that does not cause significant toxicity to the host and inhibits serotonin receptor activity. Such an amount can be determined by assessing the clinical symptoms of a patient before and after administering a fixed amount of a particular material. In addition, the pharmaceutically effective amount of a particular material administered to a host can be adjusted according to the host's response and desired outcomes. Significant toxicity can vary for each particular patient and depends on multiple factors including, without limitation, the patient's age, tolerance to pain, and disease state.

5. Identifying Inhibitors of Heart Valve Degeneration and Determining Drug Safety The invention also provides methods and materials for identifying compounds that can be used to inhibit heart valve degeneration, thrombosis, and calcification. Such methods include (a) contacting heart valve cells with a stimulant to promote proliferation, (b) contacting the proliferating cells with a test compound, and (c) determining if the test compound reduced cell proliferation. Any type of stimulant can be used provided heart valve cell proliferation is promoted. Such stimulants can include, without limitation, growth factors such as basic fibroblast growth factor, PDGF, and TGF-β as well as solutions that create hyperlipidemic conditions. In addition, any type of compound can be used as a test compound including, without limitation, polypeptides, nucleic acids, carbohydrates, lipids, synthetic chemicals, inorganic compounds, and any other compound such as those listed in the Merck Index (12th Edition, March 1996, available from the Merck Publishing Group, Rahway, N.J.). A test compound also can be a member of a combinatorial library. Compounds identified using the methods of the invention can be further evaluated, detected, cloned, sequenced, and the like.

Any method can be used to measure proliferation. For example, immunocytochemistry can be used to monitor proliferation markers such as proliferating cell nuclear antigen (PCNA). In addition, biological assays designed to detect proliferation by measuring incorporation of radiolabeled nucleotides (e.g., tritiated thymidine) can be used. Thus, a compound that inhibits heart valve degeneration can be identified by monitoring the proliferation of porcine heart valve cells stimulated with a growth factor before and after treatment with a test compound.

In another embodiment, apoptosis instead of proliferation can be used to identify therapeutic compounds. For example, a method within the scope of the invention can include (a) contacting heart valve cells with a stimulant to promote apoptosis, (b) contacting the treated cells with a test compound, and (c) determining if the test compound reduced apoptosis. Any type of stimulant can be used provided heart valve cell apoptosis is promoted. Such stimulants can include, without limitation, serotonin, fenfluramine, and cholesterol. In addition, any method can be used to measure apoptosis. For example, immunocytochemistry can be used to monitor apoptosis markers such as CPP32. In addition, a TdT-mediated dUTP-biotin nick end-labeling technique (TUNEL) can be used to measure apoptosis. Thus, a compound that inhibits heart valve degeneration can be identified by monitoring the apoptosis of porcine heart valve cells stimulated with an apoptosis-inducing factor before and after treatment with a test compound.

In addition, the methods and materials of the invention can be used to assess the safety of any substance given to a mammal. For example, any new drug designed for human use can be tested for adverse affects on heart valve tissue. In general, the substance to be tested is applied to heart valve cells after which the heart valve cells are examined for any increase in proliferation and/or apoptosis, or any change in the makeup of the extracellular matrix. Any increase in heart valve cell proliferation and/or apoptosis can indicate that the substance promotes heart valve degeneration.

The invention will be further described in the following examples, which do not limit the scope of the invention described in the claims.

EXAMPLES

Example 1

Effects of Hyperlipidemia on Heart Valve Tissue

Rabbits were used since they have a propensity to develop endothelial dysfunction when subjected to a cholesterol diet. The effects of feeding New Zealand White Rabbits a diet supplemented with 1% cholesterol (wt/wt; Purina Mills, Woodmont, Ind.) were studied. Briefly, the rabbits were fed cholesterol for ten weeks, while control rabbits received a normal diet. After ten weeks, the rabbits were anesthetized using intramuscular ketamine (68 mg/kg), xylazine (9 mg/kg), and aceprmazine (2.3 mg/kg). Heparin (100 U/kg) was administered intracardially, and the rabbits were killed four to five minutes later with an overdose of a pentobarbital sodium solution. The thorax was opened widely, and the heart removed for histologic, RT-PCR, and immunostaining analysis of the aortic heart valve. After removal, the aortic heart valves were either frozen in liquid nitrogen, or fixed in 10% formalin and embedded in parafilm. The valvular appearance, histology, and immunostaining for fibronectin were examined to determine the effects of hyperlipidemia.

Aortic heart valves from the hyperlipidemic rabbits exhibited a thickening of the valve cusp with accompanying lipid accumulation. The aortic heart valves from control rabbits did not exhibit cusp thickening or lipid accumulation. Histological evaluation of the aortic valves from hyperlipidemic rabbits revealed a definite fibroplastic proliferation of the subendothelial layer as well as a marked accumulation of lipid in what appeared to be foam cells. Similar lesions were found in the progression of atherosclerosis to advanced lesions within arteries. Aortic heart valves from control rabbits did not exhibit fibroplastic proliferation or lipid accumulation.

Fibronectin is a dimeric glycoprotein found in the extracellular matrix of most tissues. Immunostaining for fibronectin in aortic heart valves from hyperlipidemic rabbits revealed marked staining for this glycoprotein, while aortic heart valves from control rabbits exhibited very little fibronectin immunoreactivity. In addition, the fibronectin staining in aortic heart valves from hyperlipidemic rabbits was detected diffusely in the endothelial and subendothelial layer. Moreover, using RT-PCR, eNOS mRNA was detected in aortic heart valve tissue from both the hyperlipidemic and control rabbits. Taken together, these results indicate that a stimulus such as hyperlipidemia can lead to significant changes in not only the proliferative state of heart valve cells but also the molecular makeup of the extracellular matrix of heart valves.

In another experiment, osteopontin expression was evaluated. Osteopontin is a non-collagenous bone matrix protein found to be present in the hypercholesterolemic aortic valves. New Zealand rabbits (n=8) were fed with a 1% cholesterol diet for 12 weeks. Eight control animals were fed a normal chow diet. Aortic valves were cut and foam cells were identified by immunostaining for macrophage antibody. Cell proliferation was assessed by immunostaining for proliferating nuclear antigen (PCNA), and osteopontin (OP) for calcification. Transmission electron microscopy immunogold labeling confirmed osteopontin expression.

Atherosclerotic lesions were present in all cholesterol treated rabbit valves as compared to controls. These lesions stain positive for foam cell formation. There was increased osteopontin expression in the atherosclerotic lesion of the aortic valves and a thousand-fold increase in the number of proliferating cells as compared to the controls. Cholesterol levels in the rabbits: the cholesterol treated rabbits had a cholesterol level of 1036+/−96 mg/dL, the normal rabbits had a cholesterol level of 42.28 +/−mg/dL. Osteopontin expression was confirmed by immunogold labeling in the hypercholesterolemic valves. Electron microscopy analysis revealed that immunogold label is present primarily in matrix vesicles embedded in collagen fibrils which is characteristic of calcification. Further, these heavily labeled areas were enriched in cholesterol deposition.

These results indicate that hypercholesterolemia induces atherosclerotic lesions in rabbit aortic valves, as evidenced by foam cell infiltration and an increase in cellular proliferation. In addition, these results indicate that hypercholesterolemia stimulates osteopontin production. Thus, hypercholesterolemia may stimulate the calcification process present in calcific aortic valve disease.

Example 2

Effects of HMG CoA Reductase Inhibitors and Oxidative Stress on Heart Valve Tissue in vitro Valvular endothelial and subendothelial tissues were obtained from mature pigs and used to create primary explant cultures. Briefly, the cells were isolated from the cardiac aortic valves by collagenase digestion, and cultured in medium 199 with 10% (v/v) heat-inactivated fetal bovine serum at 37° C. in a humidified atmosphere of 5% $CO_2$ in air. For each experiment, the cells were used between the 3rd and 7th passage. Cells were grown to about 80 percent confluence in 24-well plates. Once at about 80 percent confluence, the cells were incubated in serum-free medium for 24 hours to arrest growth. After the 24 hour incubation, LDL (10 μg/mL) alone, pravastatin (100 nM) alone, or LDL (10 μg/mL) plus pravastatin (100 nM) was added to the wells, and the cells incubated for 18 hours. Controls were cells treated with either serum-free media or media containing 10% fetal bovine serum. Pravastatin is an HMG CoA reductase inhibitor obtained from Bristol Meyer Squibb. After the 18 hour incubation, the cells were incubated in the presence of tritiated thymidine (1 μCi/well) for four hours and a thymidine uptake assay performed to assess cellular proliferation according to the standard techniques described by Johnson et al. (*J. Mol. Cell. Card.* 19:1185–93 (1987)). Newly synthesized DNA was identified by incorporation of radioactivity into acid-precipitated cellular material. All samples were assayed in quadruplicate wells.

Treatment of the valvular cells with LDL alone resulted in substantial proliferation as compared to cells incubated in serum-free media (FIG. 1). In fact, treatment with LDL alone resulted in more proliferation than that observed for cell incubated in media containing 10% fetal bovine serum (positive control). In addition, treatment with LDL plus Pravastatin resulted in substantially less proliferation than that observed for cells treated with LDL alone. Thus, valvular cells proliferate in response to LDL, and this proliferation can be inhibited by Pravastatin.

In another experiment, cells were grown to about 80 percent confluence and then incubated in serum-free medium for 24 hours to arrest growth. After the 24 hour incubation, the cells were incubated in serum-free media containing 100 nM pravastatin for 24 hours. Control cells were incubated in serum-free media only. After the 24 hour incubation, the cultured cells were collected and homogenized in a lysis buffer (50 mM Tris-HCl, 1% NP-40, 1 mM EGTA, 1% mercaptoethanol, 100 mM leupeptin, and 1 mM PMSF). After pelleting nuclei, the supernatant was boiled in Laemmli loading buffer and separated by SDS-PAGE (7.5% acrylamide gel). Once separated, the polypeptides were electroblotted onto nitrocellulose and probed with a monoclonal antibody to endothelial nitric oxide synthase (eNOS mAb; Transduction Laboratory; Lexington, Ky.). To ensure efficient polypeptide transfer, gels were stained with Coomasie Blue.

A Western blot analysis revealed that valvular cells contain substantially more eNOS polypeptide after pravastatin treatment than that observed for cells treated with serum-free media alone. These results indicate HMG CoA reductase inhibitors can induce eNOS polypeptide expression within valvular cells.

To assess nitric oxide synthase activity, the aortic valve endothelial cell lysates were evaluated using an NADPH disphorase reaction. Briefly, each lysate was incubated for 30 minutes in a NOS assay buffer containing $^3$H-L-arginine, NADPH (100 mM), tetrahydrobiopterin (1 mM), calmodulin (10 mM), and $CaCl_2$ (25 mM). The reaction was quenched with ice cold stop buffer (2 mM EDTA, 20 mM Hepes, pH 5.5). The mixture was passed over a Dowex AG50WX-8 Na form resin and washed with one mL stop buffer. Nitric oxide synthase activity was calculated to be the amount of L-arginine converted to L-citrulline that was inhibited by 1-NAME. A scintillation counter was used to determine the amount of radioactivity.

Valvular cells treated with pravastatin exhibited about 100-fold more nitric oxide synthase activity than that observed in cells treated with serum-free media alone. Thus, HMG CoA reductase inhibitors can increase nitric oxide synthase activity in valvular cells.

Example 3

Adenoviral Vectors

Adenoviral vectors containing a cDNA encoding either β-galactosidase or eNOS were constructed using methods similar to those described by Tsutsui et al. (*Arterio. Thromb. Vascul. Biol.* 18:1231–1241 (1998). Briefly, each vector was produced by cloning the cDNA of interest into a plasmid containing a subsegment of the adenoviral genome. Each resulting construct then was cotransfected into human E1a-293 cells along with adenoviral DNA containing an E1a deletion. Adenoviruses containing a E1a deletion are replication defective, however, viral replication can occur within E1a-293 cells since these cells provide E1a products in trans. Through homologous recombination, recombinant adenoviral vectors containing the cDNA of interest were produced within the 293 cells. The recombinant adenoviral vectors were isolated and propagated. Once collected, each adenoviral vector stock was stored at −70° C. in 0.01 M Tris, 0.01 M MgCl, and 10% glycerol. The recombinant adenoviral vector containing the β-galactosidase cDNA was designated Adβgal, while the eNOS containing adenoviral vector was designated AdeNOS.

Example 4

Effects of eNOS Expression on Valvular Cell Proliferation

Valvular endothelial and subendothelial tissues were obtained from mature pigs and used to create primary explant cultures. Briefly, the cells were isolated from the cardiac aortic valves by collagenase digestion, and cultured in medium 199 with 10% (v/v) heat-inactivated fetal bovine serum at 37° C. in a humidified atmosphere of 5% $CO_2$ in air. The cells were used between the 3rd and 7th passage. For each experiment, the cells were grown to about 80 percent confluence in 24-well plates. Once at about 80 percent confluence, the cells were incubated in serum-free medium for 24 hours to arrest growth. After the 24 hour incubation, the cells were infected with either Adβgal or AdeNOS. Briefly, virus particles (206 MOI) were incubated with the cells for one hour. After the incubation, the cells were wash two times with PBS and cultured with serum-free media for 24 hours to allow expression of either β-gal or eNOS. After culturing, the cells were incubated with conditioned media for 18 hours. Control cells were incubated in either serum-free media (negative control) or media containing 10 percent fetal bovine serum (positive control). After the 18 hour incubation, the cells were incubated in the presence of tritiated thymidine (1 μCi/well) for four hours and a thymidine uptake assay performed to assess cellular proliferation according to the standard techniques described by Johnson et al. (*J. Mol. Cell. Card.* 19:1185–93 (1987)). Newly synthesized DNA was identified by incorporation of radioactivity into acid-precipitated cellular material. All samples were assayed in duplicate wells.

The conditioned media used to treat the cells was obtained from primary porcine valve explant cultures as follows. Cells were grown to confluence and then incubated for 24 hours in serum-free media. After the 24 hour incubation, 10

μg/mL of LDL was added and the cultures incubated for another 24 hours. After this second 24 hour incubation, the supernatant was collected and the cells discarded. This supernatant was used as conditioned media.

Figure 2:
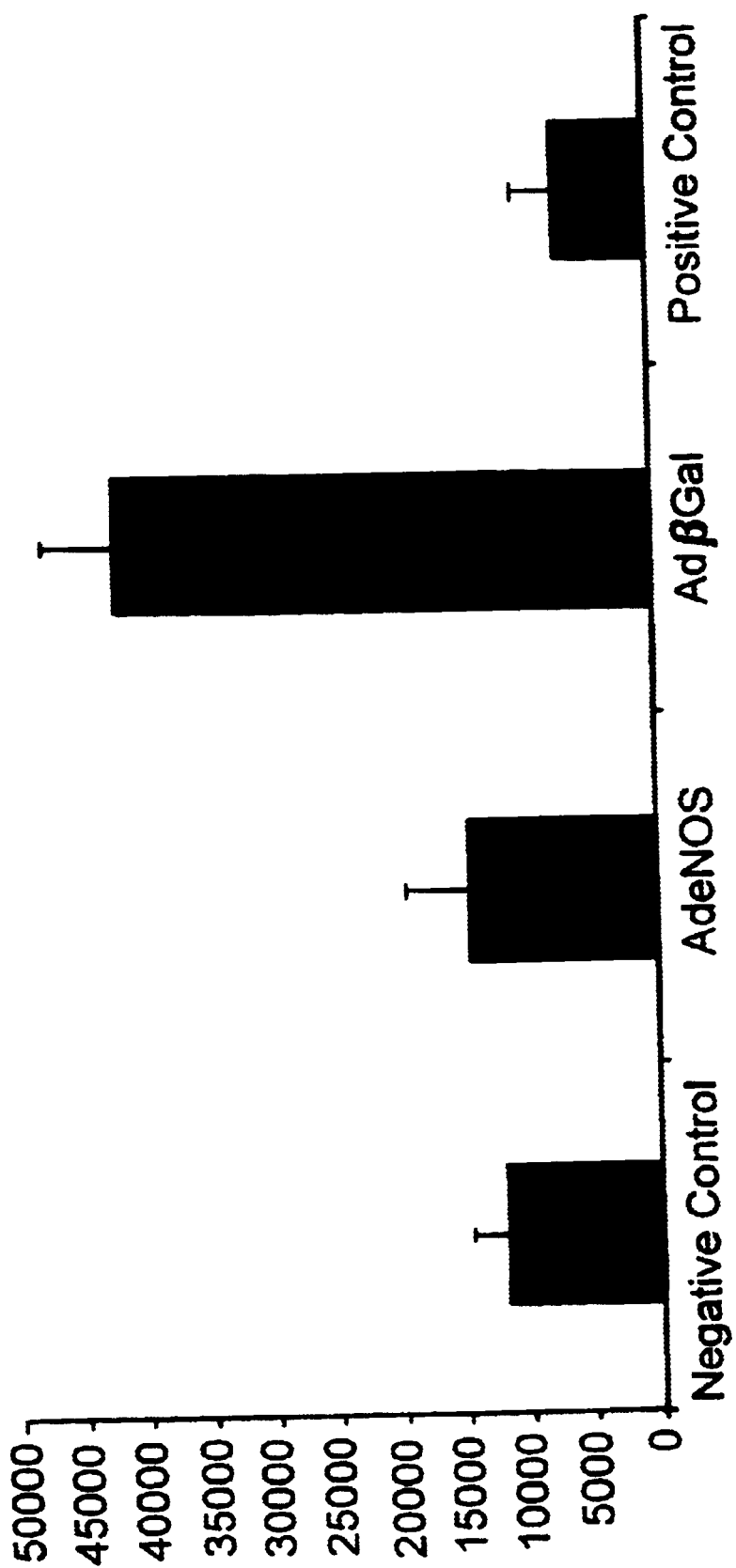
FIG. 2 is a bar graph plotting the counts per minute (cpm) for Adβgal or AdeNOS infected valvular cells treated with conditioned media. Uninfected valvular cells treated with serum-free media were used as a negative control, while uninfected valvular cells treated media containing 10% fetal bovine serum was used as a positive control.

Valvular cells infected with Adβgal and treated with conditioned media exhibited much more proliferation than that observed from similarly treated valvular cells infected with AdeNOS (FIG. 2). Thus, eNOS expression can reduce the proliferative response of valvular cells normally induced by oxidative conditions.

Example 5

Analysis of Bioprosthetic Heart Valves

Heart valve tissue is collected from porcine subjects obtained from a slaughterhouse. For human valvular tissue, a cadaver is used. Optionally, the ROSS procedure is used to remove a patient's pulmonic valve and substitute it for their aortic valve. Prior to using the human pulmonic valve, however, it is treated as described herein.

Once collected, the porcine or human heart valve tissue is stored in a cardioplegic solution oxygenated with carbogen (95% $O_2$, 5% $CO_2$). The cardioplegic solution contains 152 mM $Na^+$, 3.6 mM $K^+$, 135 mM $Cl^-$, 25 mM $HCO_3^-$, 0.6 mM $Mg^{2+}$, 1.3 mM $H_2PO_4$, 0.6 mM $SO_4^{2-}$, 2.5 mM $Ca^{2+}$, 11.2 mM glucose, 30 mM 2,3 butanedione-monoxime, and 10 IU/L insulin. The cardioplegic solution can protect the myocardium while outside a body. An adenoviral nucleic acid delivery system is used to deliver cDNAs encoding β-galactosidase and/or eNOS to the valvular endothelial cells of the heart valve tissue in vitro such that nitric oxide production can be assessed within the cells.

AdeNOS is used to infect human and porcine aortic valves. The Adβgal is used as a control to assess the degree of infection. Once infected, each tissue optionally is examined to determine the level of NOS activity using an NADPH disphorase reaction in cells. In addition, the infected tissue optionally is tested for nitrite production. Briefly, the tissue is incubated for two hours in a Krebs solution containing L-arginine (100 μM) and the calcium ionophore A23187 (1 μM; Sigma catalog number C7522) After incubation, the solution is collected and analyzed for nitrite concentration using a spectrofluorometric assay. Further, fibronectin and osteopontin production by each tissue optionally is examined using immunocytochemistry.

In another set of experiments, heart valve tissue is infected with the AdeNOS, incubated for 24–36 hours, and frozen at −70° C. Presumably, infecting the heart valve tissue with AdeNOS prior to freezing stabilizes the endothelium and extracellular matrix in addition to decreasing the amount of injury procured by the freezing process. Once thawed, the tissue is surgically implanted into a sheep or human patient. At various time points after implantation, the heart valve tissue is analyzed for degeneration, thrombosis, and calcification.

In yet another set of experiments, heart valve tissue is infected with the AdeNOS, incubated for 24–36 hours, and fixed. Presumably, infecting the heart valve tissue with AdeNOS prior to fixation stabilizes the endothelium and extracellular matrix in addition to decreasing the amount of injury procured by the fixation process. Once fixed, the tissue is surgically implanted into a sheep or human patient. At various time points after implantation, the heart valve tissue is analyzed for degeneration, thrombosis, and calcification.

Example 6

Frozen Bioprosthetic Heart Valves

Heart valve tissue is collected from porcine subjects obtained from a slaughterhouse. For human valvular tissue, a cadaver is used. Optionally, the ROSS procedure is used to remove a patient's pulmonic valve and substitute it for their aortic valve. Prior to using the human pulmonic valve, however, it is treated as described herein.

Once collected, the porcine or human heart valve tissue is stored in a cardioplegic solution oxygenated with carbogen (95% $O_2$, 5% $CO_2$). The cardioplegic solution contains 152 mM $Na^+$, 3.6 mM $K^+$, 135 mM $Cl^-$, 25 mM $HCO_3^-$, 0.6 mM $Mg^{2+}$, 1.3 mM $H_2PO_4^-$, 0.6 mM $SO_4^{2-}$, 2.5 mM $Ca^{2+}$, 11.2 mM glucose, 30 mM 2,3 butanedione-monoxime, and 10 IU/L insulin. The cardioplegic solution can protect the myocardium while outside a body. This tissue then is infected with an adenoviral vector. Briefly, an adenoviral nucleic acid delivery system is used to deliver a cDNA encoding eNOS to the valvular endothelial cells of the heart valve tissue such that nitric oxide synthase activity is increased within the cells. Once infected, the heart valve tissue is incubated for about 12 to about 36 hours (e.g., about 24–36 hours), and frozen at −70° C. This frozen heart valve tissue is thawed and implanted within a mammalian subject requiring heart valve replacement.

Example 7

Fixed Bioprosthetic Heart Valves

Heart valve tissue is collected from porcine subjects obtained from a slaughterhouse. For human valvular tissue, a cadaver is used. Optionally, the ROSS procedure is used to remove a patient's pulmonic valve and substitute it for their aortic valve. . Prior to using the human pulmonic valve, however, it is treated as described herein.

Once collected, the porcine or human heart valve tissue is stored in a cardioplegic solution oxygenated with carbogen (95% $O_2$, 5% $CO_2$). The cardioplegic solution contains 152 mM $Na^+$, 3.6 mM $K^+$, 135 mM $Cl^-$, 25 mM $HCO_3^-$, 0.6 mM $Mg^{2+}$, 1.3 mM $H_2PO_4^-$, 0.6 mM $SO_4^{2-}$, 2.5 mM $Ca^{2+}$, 11.2 mM glucose, 30 mM 2,3 butanedione-monoxime, and 10 IU/L insulin. The cardioplegic solution can protect the myocardium while outside a body. This tissue then is infected with an adenoviral vector. Breifly, an adenoviral nucleic acid delivery system is used to deliver a cDNA encoding eNOS to the valvular endothelial cells of the heart valve tissue such that nitric oxide synthase activity is increased within the cells. Once infected, the heart valve tissue is incubated for about 12 to about 36 hours (e.g., about 24–36 hours), and fixed. This fixed heart valve tissue is implanted within a mammalian subject requiring heart valve replacement.

Example 8

Carcinoid Heart Disease

Heart valve tissue was obtained from patients with and without carcinoid heart disease. Patients with carcinoid heart disease were identified by retrospective review of a tissue registry. In addition, patients were identified as having carcinoid heart disease by measuring 5-HIAA levels within urine as well as by histologically examining heart valve tissue for a normal endothelial layer and a subendothelial layer containing proliferating cells and an increased extracellular matrix.

Gross inspection of the heart valves from patients with carcinoid heart disease at the time of valve replacement reveal a smooth appearing endocardial surface. In addition, these heart valves contained plaque-like lesions consisting of a thickened subendothelial cell layer. In fact, these subendothelial cells compose the majority of the endocardial plaque surface. Conversely, normal control heart valves exhibited a clear, glistening valvular cusp with no visible evidence of endocardial plaque lesions. The valve surface was intact.

To examine collagen synthesis, the heart valves were stained with Masson trichrome. A marked increase in the collagen identified by the Masson trichrome stain was observed in the carcinoid valves as compared to the normal valves. In addition, younger lesions exhibited less blue intensity than older lesions indicating that younger lesions have a lesser amount of collagen synthesis than the older lesions.

PCNA immunostaining was performed to examine in situ proliferation ex vivo. Briefly, slides containing the heart valve tissue were deparaffinized and rehydrated through the following solutions: xylene twice for five minutes, 100% ethanol twice for ten seconds, and 95% ethanol twice for ten seconds. Endogeneous peroxidase activity was blocked by incubating the slide in a 50% volume $H_2O$/50% volume methanol solution at room temperature for ten minutes followed by a rinsing with running tap water. Non-specific polypeptide binding sites were blocked by applying 5% normal horse serum diluted in PBS/0.05% Tween 20 (pH 7.2–7.4; obtained from Pierce Chemical Co.) to each slide for ten minutes at room temperature. The serum was blotted off, and primary antibody diluted in 1% normal horse serum plus PBS/0.05% Tween 20 applied for an overnight incubation period in a humidity chamber at 4° C. The PCNA antibody (obtained from Dako; Carpinteria, Calif.) was used at a 1:7500 dilution. As described below, the heart valve tissue also was stained with an $5HT_{1B}$ antibody (1:75 dilution; obtained from Santa Cruz Biotech; Santa Cruz, Calif.). After overnight incubation, the primary antibody was rinsed off with tap water, the slides blotted, and a biotinylated secondary antisera cocktail containing goat anti-mouse IgG (diluted 1:400) added. After a 30 minute room temperature incubation, the slides were rinsed with running tap water, and incubated with streptavidin-horseradish peroxidase diluted 1:500 in PBS/0.05%, Tween 20 with 1% normal goat serum for 30 minutes at room temperature. The slides then were rinsed with running tap water, and exposed to color development using 3-amino-9-ethylcarbazole as a substrate solution (Sigma) for 15 minutes at room temperature. The slides were counterstained with hematoxylin for 30 seconds, and a coverslip applied.

PCNA quantitation was performed by automated digital image analysis. Immunoperoxidase stains treating the tissue were measured by comparing intensity of light passing through the glass slide on which the cells reside. This light was captured by a video camera set at a specific wavelength. The absorption value of each pixel represents the level of light absorbed by the cellular constituents in a finite area. These pixels were then quantified for the analysis of proliferating cellular nuclei.

PCNA immunostaining of heart valves from carcinoid heart disease patients revealed a marked increase in the number of positive brown staining nuclei as compared to normal control tricuspid valves, corresponding to an upregulation of DNA polymerase in the carcinoid valves. It is noted that DNA polymerase is a marker of cell proliferation. Quantitation of the number of PCNA positive staining nuclei in the carcinoid tricuspid valve versus the normal tricuspid valve revealed a 35-fold increase in the number of positive nuclei as compared to the control (p<0.001).

In addition, heart valves from carcinoid heart disease patients exhibited a marked increase in the number $5HT_{1B}$ receptor positive cells when compared to number of $5HT_{1B}$ receptor positive cells detected in normal control tricuspid valves.

To examine the direct proliferative effects of serotonin, cultured porcine aortic valve subendothelial cells were treated with 1 μM, 100 nM, and 10 nM of serotonin and then tested using a $^3H$ thymidine incorporation assay. Serotonin treatment markedly increased cell proliferation in the subendothelial cells as compared to untreated cells (33-fold, p<0.001). Incubation with serotonin and a $5HT_{1B}$ receptor antagonist, methiothepin (7 nM), inhibited the serotonin-induced proliferation.

These results indicate that serotonin is a powerful direct mitogen on subendothelial valve cells, and that this mitogenic effect is, at least in part, mediated via $5HT_{1B}$ receptors. Thus, $5HT_{1B}$ receptor antagonists such as pindolol, cyanopindolol, 5-HT-moduline, and methiothepin can be used to treat carcinoid heart disease.

Human valve tissue was also stained with sirius red, which stains collagen I, as described elsewhere (Dayan et al., *Histochem.* 93:27–29 (1989)). Briefly, slides containing human valve tissue were deparaffinized and rehydrated through the following solutions: xylene twice for five minutes, 100% ethanol twice for ten seconds, and 95% ethanol twice for ten seconds. After rehydration, the slides were incubated for one hour at room temperature in 0.1 percent sirius red solution. The 0.1 percent sirius red solution contained 0.1 g direct red 80 (Sigma, catalog number D0303) in 100 mL of saturated picric acid. After the one hour incubation, the slides were incubated in one percent acetic acid for 30 minutes, rinsed with distilled water for ten seconds three times, and counterstained with hematoxylin for 20 seconds. The one percent acetic acid contained one mL of glacial acetic acid in 99 mL distilled water. After counterstaining, the slides were treated with acid alcohol, rinsed with tap water, dehydrated through alcohols, cleared in xylene, and mounted. The acid alcohol contained one mL hydrochloric acid, 29 mL distilled water, and 70 mL 100% ethanol.

Sirius red staining revealed a qualitative increase in collagen I staining in carcinoid heart valve tissue as compared to normal heart valve tissue.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated heart valve cusp, wherein a cell of said cusp contains an exogenous nucleic acid that encodes a nitric oxide synthase, and wherein said cell expresses said nitric oxide synthase and has a reduced susceptibility to calcification.

2. The cusp of claim 1, wherein said cell is porcine.

3. The cusp of claim 1, wherein said cell is human.

4. The cusp of claim 1, wherein said nitric oxide synthase is an endothelial nitric oxide synthase.

5. A method for making a bioprosthetic heart valve cusp, said method comprising:

a) obtaining a heart valve cusp, and b) introducing nucleic acid into a cell of said cusp, wherein said nucleic acid encodes a nitric oxide synthase, and wherein said cell expresses said nitric oxide synthase and has a reduced susceptibility to calcification.

6. The method of claim 5, wherein said cell is porcine.

7. The method of claim 5, wherein said cell is human.

8. The method of claim 5, wherein said nitric oxide synthase is an endothelial nitric oxide synthase.

9. The method of claim 5, wherein said nucleic acid is introduced into said cell via adenoviral-mediated nucleic acid transfer.

10. The method of claim 5, wherein said nucleic acid integrates into the genome of said cell.

11. The method of claim 5, wherein said method comprises fixing said cusp.

12. The method of claim 11, wherein said fixation step occurs after said introduction step.

13. The method of claim 5, wherein said method comprises freezing said cusp.

14. The method of claim 13, wherein said freezing step occurs after said introduction step.

15. A method for providing a mammal with a non-murine heart valve, said method comprising:
   a) providing an isolated non-murine heart valve;
   b) introducing a nucleic acid encoding a nitric oxide synthase into a cell of said heart valve such that said cell expresses said nitric oxide synthase, and
   c) introducing said heart valve of step (b) into said mammal, wherein said heart valve is an autograft or allograft.

16. The method of claim 15, wherein said method comprises administering an inhibitor of hydroxymethylglutaryl coA reductase activity to said mammal.

17. The method of claim 16, wherein said inhibitor comprises pravastatin, atorvastatin simvastatin or lovastatin.

18. A method for providing a mammal with a non-murine heart valve, said method comprising:
   a) providing an isolated non-murine heart valve;
   b) introducing a nucleic acid encoding a nitric oxide synthase into a cell of said heart valve such that said cell expresses said nitric oxide synthase,
   c) fixing or freezing said heart valve of step (b), and
   d) introducing said heart valve of step (c) into said mammal, wherein said heart valve is a xenograft.

19. The method of claim 18, wherein said method comprises administering an inhibitor of hydroxymethylglutaryl coA reductase activity to said mammal.

20. The method of claim 19, wherein said inhibitor comprises pravastatin, atorvastatin, simvastatin, or lovastatin.

* * * * *

UNITED STATES PATENT AND TRADEMARK OFFICE
CERTIFICATE OF CORRECTION

PATENT NO. : 6,660,260 B1
DATED : December 9, 2003
INVENTOR(S) : Nalini M. Rajamannan It is certified that error appears in the above-identified patent and that said Letters Patent is hereby corrected as shown below:

Title page,
Item [56], References Cited, OTHER PUBLICATIONS, "Kullo et al." reference, please delete "," after "Arterio" and insert -- . -- therefor.

Column 22,
Line 8, after "atorvastatin" please insert -- , --;
Line 8, after "simvastatin" please insert -- , --.

Signed and Sealed this

Twenty-ninth Day of June, 2004

JON W. DUDAS
*Acting Director of the United States Patent and Trademark Office*